United States Patent [19]

Boyle et al.

[11] Patent Number: 5,071,756

[45] Date of Patent: Dec. 10, 1991

[54] BACTERIAL FC RECEPTORS

[75] Inventors: Michael D. P. Boyle, Gainesville, Fla.; Michele Yarnall, Pullman, Wash.

[73] Assignee: University of Florida, Gainesville, Fla.

[21] Appl. No.: 330,763

[22] Filed: Mar. 30, 1989

Related U.S. Application Data

[62] Division of Ser. No. 836,743, Mar. 6, 1980, Pat. No. 4,883,754.

[51] Int. Cl.$^5$ .............................................. C07K 15/04
[52] U.S. Cl. ..................................... 435/177; 424/1.1; 424/88; 435/188; 530/380; 530/387; 530/388; 530/812; 530/825; 530/350; 530/389; 530/391
[58] Field of Search ............... 530/350, 380, 387, 388, 530/812, 825, 389, 391; 435/177, 188; 424/1.1, 88

[56] References Cited

U.S. PATENT DOCUMENTS 3,850,798 11/1974 Sjoquist .......................... 530/387 X
4,883,754 11/1989 Boyle et al. ......................... 435/177

OTHER PUBLICATIONS

Molecular Immunology, 17, 1563-1573 (1980), Myhre et al.
Eur-J. Biochem. 29, 572-578 (1982), Sjoquist et al.
International Archs. Allergy Appl. Immunol. 62, 369 (1982) Grubb et al.

Primary Examiner—Howard E. Schain
Attorney, Agent, or Firm—Saliwanchik & Saliwanchik

[57] ABSTRACT

A type II, proteinaceous, antigenic factor derived from a Group A streptococci which is a receptor for the Fc region of human Ig G3 and which exhibits a major diffuse protein band on polyacrylamide gel electrophoresis and which has a molecular weight of about 38,000 daltons.

6 Claims, 9 Drawing Sheets

BACTERIAL FC RECEPTORS

BACKGROUND OF THE INVENTION

Work leading to the present invention was supported by NIH Grant A120445. The United States Government has certain rights in this invention.

This is a divisional of Application Ser. No. 836,743, filed Mar. 6, 1986, now U.S. Pat. No. 4,883,754.

The present invention relates to certain novel bacterial receptors that bind to the Fc region of immunoglobulin and methods for their preparation.

THE PRIOR ART

It has been recognized for years that the surface of streptococci and staphylococci bacteria contain proteins or factors which are reactive with, i.e., bind to the Fc region of all or some of the subclasses of human and animal immunoglobulin. See Langone, Adv. Immunol. Vol. 32, p. 167 (1982); and Myhre et al, pp. 209-210, Holm & Christensen (eds.), Basic Concepts of Streptococci and Streptococcal Diseases, Redbook Ltd., Chertsey, Surrey (1984) for a discussion of these factors referred to herein as Fc receptors. The majority of surface Fc-receptor-positive staphylococcal strains also secrete Fc receptors during culture [Langone, supra]. By contrast, none of the Fc-positive streptococcal strains have been found to secrete significant quantities of a soluble receptor [Myhre et al, supra; Reis et al, J. Immunol. Methods, Vol. 59, p. 83 (1983)]. Functional studies of their reactivity with different species and subclasses of IgG have suggested that five distinct types of bacterial Fc receptor activities exist. These have been designated by Myhre & Kronvall, supra, as types I to V. The type-I receptor, staphylococcal protein A, is the most extensively studied bacterial Fc receptor and has been isolated to functional and physiochemical homogeneity [Sjoquist et al, Eur. J. Biochem., Vol. 29, p. 572 (1972)].

The type II receptor is found on few group A streptococcus [Myhre et al, Mol. Immunol., Vol. 17, pp. 1563-1573 (1980)]. The type III receptor is found on the majority of human group C and group G strains of streptococcus [Myhre et al, ibid.]. The type IV receptor is found in certain bovine group G streptococci [Myre et al, Basic Concepts of Streptococci and Staphylococcal Diseases, Holm, S. E. and Christensen, P. eds., pp. 209-210 Reed Books, Ltd. Chertsey, Surrey (1981)]. The type V receptor is found on certain strains of Streptococcus zooepidemicus [Myhre et al, Infect. Immun., Vol. 27, pp. 808-816 (1980)].

Attempts to isolate the other four types of bacterial Fc receptors have met with varying degrees of success [Christensen et al, Acta. Path. Microbiol. Scand. [C[, Vol. 84, p. 196 (1976); Grubb et al, Int. Arch. Allergy Appl. Immunol., Vol. 67, p. 369 (1982); and Havlicek, Ex. Cell. Biol., Vol. 46, p.146 (1978)]. Recently there have been described methods for measuring cell surface and secreted Fc-receptor activity [Reis et al, supra]. These methods have resulted in the identification of a group C streptococcal strain which expreses a level of Fc-receptor activity similar to that of the protein A-rich Staphylococcus aureus Cowan strain and the isolation of a functionally homogeneous Fc receptor that has the properties of a type-III receptor [Reis et al, J. Immunol., Vol., 132, p. 3091 (1984)].

The Fc region of immunoglobulins plays an important role in directing the effector functions of antibodies [Calvanico et al, Immunochemistry of Proteins, Vol. 3, pp. 1-85 (1979)]. Bacterial Fc receptors, in particular the type I Fc receptor (staphylococcal protein A), have proved to be of great value for studying the fine structure of the Fc region of human immunoglobulins [Recht et al, J. Immunol., Vol. 127, 917-923 (1981); Shimuzu et al, Mol. Immunol., Vol. 20, p. 141-148 (1983); Haake et al, J. Immunol., Vol. 129, p. 190-192 (1982)]. Analysis of the protein-A-IgG interaction has demonstrated that when histidine is substituted for arginine at position 435 of the heavy chain a non-reactive IgG3 molecule acquires the ability to bind protein A [Recht et al, supra; Shimizu et al, supra; and Haake et al, supra].

The type II Fc receptor on group A streptococci and the type III Fc receptor, found on the majority of group C and Group G streptococci, have been reported to react with all four human IgG subclasses [Myrhe et al, supra; Reis et al, Scand. J. Immunol., Vol. 20, p. 433-439 (1985); Reis et al, J. Immunol.., Vol. 32, p. 3098-3102 (1984); Bjorck et al, J. Immunol., Vol. 133, p. 964-974 (1984); and Reis et al, supra].

The lack of a readily available Fc receptor which selectively and exclusively reacts with $IgG_3$ antibodies has severely hampered efforts to isolate and quantitate human $IgG_3$.

It is an object of the present invention to provide certain novel bacterial Fc receptors, including one which is selective for human $IgG_3$ and methods for their preparation.

SUMMARY OF THE INVENTION

According to the invention there is provided a type II proteinaceous, antigenic factor derived from a group A streptococcus which is a receptor for the Fc region of human $IgG_3$ and which exhibits a major diffuse protein band on polyacrylamide gel electrophoresis and has an apparent molecular weight of about 38,000 daltons.

The present invention also provides a type II proteinaceous antigenic factor derived from a group A streptococcus which is a receptor for the Fc region of human $IgG_1$, $IgG_2$ and $IgG_4$ and which exhibits a major diffuse protein band on polyacrylamide gel electrophoresis and has a molecular weight of approximately 56,000 daltons.

The present invention also provides a method for preparing the above factors comprising:

1) solubilizing the factors from a group A streptococcus, 2) purifying the factors by affinity chromatography on an appropriate immobilized IgG sub-class and 3) separating the factors.

DETAILED DESCRIPTION OF THE INVENTION

The factors of the invention may be prepared from any Group A streptococcal strain, e.g., those designated Nos 209, Hu 13, 670, 1130, 7209, B920, B512, A992, A928, A547, B905, B438, B575, etc. The characteristics of each of these strains are described in detail by Reis et al, J. Immunol. Methods, Vol. 59, pp. 83-94 (1983); Reis et al, Scand. J. Immunol., Vol. 20, pp. 433-439 (1984); Yarnall et al, J. Microbiol. Methods, Vol. 3, pp. 83-93 (1984), the disclosures of which are incorporated herein by reference.

Prior to preparing the factors from the group A streptococcus it is preferred to increase the Fc-receptor expression thereof by serial passage in an appropriate animal, e.g., mouse, according to the method of Reis, Yarnall, Ayoub and Boyle, Scand. J. Immunol., Vol. 20, pp. 433-439 (1984), the disclosure of which is incorporated by reference herein. A preferred strain is that designated 64/14, i.e., the strain isolated from the fourteenth passage of strain 64 through mice according to the method of Reis et al, supra.

It is further preferred to further select from this strain using the immunoblotting technique described by Yarnall et al, J. Microbiol. Meth., Vol. 3, pp. 83-93 (1984), the disclosure of which is incorporated herein by reference. This preferred selected strain is designated herein as 64/14/HRP (high receptor positive). The blotting technique is used to select the highest Fc receptor expressing colonies from within an isolate of the mouse passaged 64/14 strain.

The factors of the invention may be prepared from the passaged strain by any one of a variety of extraction procedures. For example, the factors may be derived from the strains by mutanolysin or hyaluronidase extraction, papain or trypsin digestion, phage lysin, SDS or autoclave treatment or acid, alkaline or heat extraction according to the following protocols.

The selected group A streptococcal strain, e.g., 64/14/HRP was grown overnight at 37° C. in Todd-Hewitt broth. Approximately 6 g (wet weight) of bacteria were recovered from 3 liters of Todd-Hewitt broth.

Mutanolysin extraction. Approximately 6 g (wet weight) of group A strain 64/14/HRP were suspended in 30 ml of 20 mM Tris-HCl, pH 7.5, 1 mM idoacetic acid, and 1 mM benzamidine HCl. To this suspension, 100 µg/ml pancreatic DNase (Sigma), 100 µg/ml pancreactic RNase (Sigma), and 100 µg/ml mutanolysin were added. A commercial mutanolysin preparation (Sigma) was further purified to remove protease activity using the method described by Sieghel et al, Infect. Immun., Vol. 31, pp. 808-815 (1981). The enzyme and bacteria were incubated at 37° C. in a shaking water bath for 4 hr. The mixture was then centrifuged at 10,000 g for 10 min. and the resulting supernatant filtered through a 0.2 µm filter to remove the remaining bacteria. The filtrate was dialyzed against 20 mM Tris-HCl, pH 7.5 containing 1 mM iodoacetic acid, 1 mM benzamidine-HCl, and 1 mM benzamidine-HCl, and 1 mM phenylmethyl sulfonyl fluoride (PMSF).

Hyaluronidase extraction. Approximately six grams (wet weight) of the group A strain, 64/14/HRP, were suspended in 30 ml of 0.15 M phosphate buffered saline, pH 7.2 (PBS). To this suspension, 10 mg type IV hyaluronidase (Sigma) was added and incubated at room temperature for 30 min. The bacteria free supernatant was recovered as described above.

Papain digestion. Group A strain 64/14/HRP, approximately 2 g (wet weight), was suspended in 20 mls of 10 mM Tris-HCl, pH 8.0 and 0.02% NaN$_3$. Two milliliters of 0.4 M cysteine and 1.6 mg papain were added to this suspension and allowed to incubate at 37° C for 1 hr. The reaction was stopped by addition of iodoacetic acid to a final concentration of 30 mM. The bacteria free supernatant was recovered as described above.

Trypsin digestion. Approximately 2 grams (wet weight) of group A strain 64/14/HRP in 50 mM KPO$_4$, 5 mM EDTA, 0.02% NaN$_3$, pH 6.1 (20 ml) was incubated at 37° C. for 1 hr. with 80 µg pancreatic DNase and 400 µg trypsin (Sigma). Addition of benzamidine-HCl to a final concentration of 100 mM stopped the reaction. Bacteria were removed as described above.

Phage lysin treatment. Approximately 2 g (wet weight) of the group A strain 64/14/HRP were suspended in 20 ml of 50 mM KPO$_4$, 5 mM EDTA, 0.02% NaN$_3$, pH 6.1. Phage lysin (0.2 ml), previously activated by incubation at room temperature for 15 min. in dithiothreitol (DTT) at a final concentration of 50 mM, was added to the 10% suspension and incubated at 37° C. for 1 hr. The phage lysin was prepared as described by Fischetti et al, J. Exp. Med., Vol. 133, pp. 1105-1117 (1971). The bacteria free supernatant was recovered as decribed above.

SDS treatment. A 10% (w/v) suspension of group A strain 64/14/HRP in 1% sodium dodecyl sulfate was incubated at 80% for 10 min. Bacteria were removed as described above and SDS was removed by dialysis against 20 mM Tris-HCl, pH 7.5.

Autoclave treatment. A 10% (w/v) suspension of group A strain 64/14/HRP was autoclaved at 124° C. for 15 min. with or without the addition of 1% SDS.

Hot acid/hot alkaline extractions. These extractions were carried out according to the method of Lancefield, J. Exp. Med., Vol. 47, pp. 91-103 (1928). Bacteria were suspended in 0.15M PBS to form a 10% suspension and the pH was adjusted to 2 (or 10) with 0.5M HCl (or 0.5 M Na OH). The bacterial suspension was boiled for 10 min and the pH neutralized. The bacteria free supernatants were recovered as described previously.

Heat extraction. This procedure is carried out as described above, but at neutral pH using PBS, pH 7.0.

Following extraction the respective IgG$_3$ specific and IgG$_1$, IgG$_2$ and IgG$_4$ specific factors are purified by affinity chromatography on immobilized IgG according to the general method outlined in U.S. Pat. No. 3,850,798, the disclosure of which is incorporated by reference herein. Thus, the IgG$_3$ specific factor of the invention is isolated by binding to and elution from immobilized IgG$_3$. The IgG$_1$, IgG$_2$ and IgG$_4$ specific factors are isolated and purified by binding to and elution from immobilized IgG which has been depleted of IgG$_3$ by extensive absorption with Protein A-sepharose. The method utilizes an appropriate human IgG sub-class covalently immobilized on any suitable substrate, e.g., of Afi-gel 10, Afi-gel 15, cyanogen bromide activated Sepharose, or other conventional support material, to isolate the factors. It will be understood, however, that any species of IgG, including rabbit and pig, to which the factor binds may be employed.

Following purification and isolation, the factors are preferably concentrated to from about 40 µg/ml to about 400 µg/ml by e.g., ultrafiltration using an Amicon ultrafiltration device with a molecular weight cut-off of 10,000 daltons, and separated from each other by polyacrylamide gel electrophoresis.

The receptor specific for IgG$_3$ is exceptionally useful for the isolation, detection and quantitation of antibodies of the IgG$_3$ sub-class in man. Sub-class restricted responses in various diseases such as Brucella infection in humans, are characteristic of the disease state. Thus, the ability to measure sub-class responses selectively is of clinical value in diagnosis and assessment of the immune status of patients. Thus, the factor has considerable application as a research reagent and clinical screening agent.

The factor specific for IgG$_1$, IgG$_2$ and IgG$_4$ is similarly useful for the detection, isolation and quantitation of those sub-classes of IgG.

The factors may be labelled for the above uses according to the methods outlined in the copending patent application of Boyle et al, supra, with radioisotopes, e.g., $125_I$, $131_I$, $3_H$, $14_C$, $35_S$, etc; enzymes, e.g. lactoperoxidase, horse-radish peroxidase, alkaline phosphatase, glucose oxidase, etc.; or electron dense ligands, e.g. ferritin, gold, etc. The factors may also be immobilized on inert supports such as Afi-gel 10, Afi-gel 15, immunobeads, cyanogen bromide activated Sepharose, Afi-gel 701, 702, etc. for use as immunological reagents.

In the following examples, the factors of this invention were prepared and compared with other types of receptors.

In the Examples, Staphylococcus aureus Cowan I strain served as a representative type I Fc receptor. The group C streptococcal strain 26RP66 served as a type III receptor-positive strain. All strains were grown in Todd-Hewitt broth (DIFCO) as stationary cultures for 18-24 hours at 37° C., harvested by centrifugation and resuspended in phosphate-buffered saline (PBS), pH 7.2. The optical density at 550 nm was determined to standardize the concentration of organisms used in the tests. An $OD_{550}$ of 0.3 corresponds to approximately $2 \times 10^9$ organisms/ml.

The type I receptors referred to herein were purchased from commercial sources.

The type III receptors were isolated by trypsinizaton.

A homogeneous form of the type III Fc receptor is extracted from the group C streptococcal strain 26RP66 by selection of appropriate conditions for trypsin treatment (e.g., 1.5 hours at 37° C. in 0.05 M $KH_2PO_4$, 0.005 M EDTA, pH 6.1 trypsin concentration (20 μg/ml. The Fc receptor activity in the resulting cell free extract was then purified by binding to, and elution from, a column of immobilized human IgG as described herein.

In the examples, the following procedures were employed.

Immobilized IgG preparations.

Antigens were coupled to immunobeads by the method described by Reis et al, J. Immunol. Methods, Vol. 59, pp. 83-94 (1983). The ligand to be immobilized was covalently bound to the immunobead matrix by peptide bond formation between the carboxylic groups on the beads and amino acids groups of the ligand. This reaction is catalyzed by carbodiimide and the resulting beads can be stored for up to six months at 4° C. in the presence of 0.02% sodium azide without loss of reactivity.

Immobilized IgG for affinity purification of the streptococcal Fc receptor was prepared by covalently coupling human IgG to the high capacity affi-gel 15 beads (Bio-Rad) as described by Reis et al, J. Immunol., Vol. 132, pp. 3091-97 (1984)

Iodination of IgG and Protein A.

Purified protein A (Pharmacia) or purified human IgG was iodinated by mild lactoperoxidase method using enzyme beads (Bio-Rad) as described by Reis et al (1982), ibid. The IgG or protein A routinely had a specific activity of 0.3 mCi/mg.

Preparation of Fc specific probe.

$125_I$ labeled human IgG was made Fc specific by the inclusion of a twofold molar excess of unlabled $F(ab')_2$ fragments in the probing mixture. Human IgG $F(ab')_2$ fragments were prepared by pepsin digestion of the stock IgG preparation by the method described by Reis et al, supra. The I9G and $F(ab')_2$ fragments were prepared from an individual donor and consequently the IgG and $F(ab')_2$ fragments contained the same distribution of antigenic reactive antibodies. Therefore, only binding via the Fc region is measured using this probing mixture.

Competitive binding assay for soluble bacterial Fc receptor.

Fc receptor activities in extracts were quantified using the competitive binding assay of Reis et al, ibid. This assay was carried out using VBS-gel as the diluent. In this assay 1.0 ml of a test sample or buffer was mixed with 0.1 ml of a standard suspension of agarose beads with covalently coupled human IgG, and 0.1 ml of $125_I$ protein A (approximately 20,000 cpm) and incubated at 37° C. for 90 min. Two milliliters of veronal buffered saline containing 0.01 M trisodium ethylenediamine tetra-acetate and 0.1% gelatin (EDTA-gel) was added to each tube and centrifuged at 1,000 g for 5 min. and the supernatant fluid decanted. After an additional wash, the radioactivity associated with the beads was determined in an LKB Gamma Counter.

Preparation of monospecific antibodies to a single species of affinity purified Fc-reactive material.

Monospecific antibodies were prepared in chickens whose non-immune IgG does not react with the Fc-receptor protein being studied. The choice of a non-reactive host to immunize is important to avoid complications with hypersensitivity and Arthus reactions. Immunoglobulins were isolated from egg yolks as described below. Eggs from a white Leghorn chicken were collected prior to injection with isolated Fc-reactive protein. This provided a source of pre-immunization IgG from an individual animal which was used as a control for later studies. The chicken was then injected with an immunogen containing approximately 50 μg of Fc-reactive material intramuscularly or subcutaneously in complete Freund's adjuvant. The immunogen used was a single form of the Fc-receptor protein that was isolated first by affinity purification by binding to and elution from a column of immobilized IgG and then further purified by SDS polyacrylamide gel electrophoresis. The gel was stained with Coomassie blue, and a single stained band was cut from the gel, emulsified in adjuvant and used as the immunogen. The chickens were allowed to rest for three weeks and then injected with approximately 50 μg of the immunogen prepared as described above and that had been emulsified in incomplete Freund's adjuvant Eggs were collected from the chickens, immunoglobulins were extracted, and the production of antibody was monitored as described below.

Chloroform extraction of egg yolks

Eggs from the chicken were extracted using a modification of the procedure described by Auliso Proc. Soc. Exp. Med., Vol. 125, pp. 312-315 (1967). The yolks were separated from the albumin and adhering membrane, diluted with an equal volume of PBS, and shaken several times. The suspension stood at room temperature for 10 min. The extraction was repeated a total of 4 times before centrifugation at 10,000 g for 20 min. To the supernatant, an equal volume of chloroform was added and the mixture was shaken at room temperature every 30 min. for 2 hours before incubating at 4° C. overnight. The extraction was centrifuged at 5,000 g for 10 min. The resulting clear supernatant was assayed for antibody production by measuring the inhibition of $^{125}$I labeled human IgG binding to the type II receptor rich group A bacterial strain, 64/14/HRP.

Chicken anti-type I and anti-type III antibodies

Monospecific antiserum to the staphylococcal type I Fc receptor was prepared as described by Reis et al, J Clin. Lab. Immunol., Vol. 13, pp. 75-80 (1984). Monospecific antiserum to the streptococcal type III Fc receptor was prepared as described by Reis et al, J. Immunol , Vol. 132, pp. 3091-97 (1984).

Immobilized anti-type II Fc receptor

Anti-type II Fc receptor antibodies isolated from chloroform extracted egg yolks were concentrated by ammonium sulfate precipitation (40%) and covalently coupled to affi-gel 15 activated beads (Bio-Rad) as described above. The immobilized anti-type II Fc receptor was used for the affinity purification of the type II Fc receptor.

Purified type I and type III Fc receptors

Purified type I Fc receptor (protein A) was obtained commercially. The type III Fc receptor was purified as described by Reis, et al, J. Microbiol. Method Vol. 4, pp. 45-58 (1985).

Solubilization of the type II Fc receptor.

The mouse-passaged group A streptococcal strain, 64/14/HRP described above, was selected because of its high levels of surface Fc receptors and its stability on subculture. Several of the above described extraction procedures were compared including: 1) hot-acid extraction, alkaline extraction, or heat extraction at neutral pH, 2) treatment with the enzymes hyaluronidase, mutanolysin, papain, trypsin, or phage lysin, or 3) heating or autoclaving the bacteria in the presence of sodium dodecyl sulfate (SDS). The resulting cell free extracts were tested for soluble Fc receptor activity using two assays. The first was a competitive binding assay that measures the inhibition of $^{125}$I labeled protein A (the type I Fc receptor) to immobilized human IgG and is capable of detecting nanogram quantities of Fc-reactive proteins.

The second assay was a Western blotting procedure. In this procedure, the extractions were electrophoresed on an SDS polyacrylamide gel, electroblotted onto nitrocellulose, and probed with the $^{125}$I labeled human IgG Fc specific probe. By running a duplicate gel and staining with Coomassie brilliant blue, Fc receptor activity can be matched to specific protein bands. The Western blotting procedure has a number of advantages First, it enabled size heterogeneity of Fc receptors to be detected and second, it detected Fc reactivities with sites on IgG not related to the binding site for staphylococcal protein A.

The only treatments that resulted in the solubilization of significant quantities of Fc receptor activity were heat extraction at neutral pH, and treatment with the enzymes mutanolysin or hyaluronidase (Table I). Extraction with SDS or autoclaving in the presence of SDS also resulted in solubilizing Fc receptor activity, but with lower specific activity. Extraction of the group A streptococci with acid, alkali, papain, trypsin, phage lysin, or by autoclaving did not solubilize detectable quantities of a functionally active Fc receptor in either assay. Comparison of the extracts by Western blot analysis showed that the extract with the least heterogeneity resulted from heating the bacteria at neutral pH. This extraction procedure was consequently used to isolate the type II Fc receptor.

TABLE I

| Extraction | Yield (μg/g bacteria) | Western Blot Analysis (Number of protein bands) | Competitive Binding Assay (μg required for 50% inhibition) |
| --- | --- | --- | --- |
| Heat | 36 | 2 | 1.5 |
| Hot acid | — | None | No inhibition |
| Hot alkaline | — | None | No inhibition |
| Hyaluronidase | 24 | 4 | 8.4 |
| Mutanolysin | 115 | 8 | 0.2 |
| Papain | — | None | No inhibition |
| Trypsin | — | None | No inhibition |
| SDS | — | 7 | 200 |
| Autoclaving | — | None | No inhibition |
| Autoclaving + SDS | — | 5 | 200 |
| Phage lysin | — | None | No inhibition |

Isolation of the type II Fc receptor

The type II Fc receptor rich group A streptococcus was heat extracted as described in the Methods. The bacteria free extract was dialyzed against 20 mM Tris-HCl, pH 7.5 containing protease inhibitors at a concentration of 1 mM phenylmethyl sulfonyl fluoride (PMSF), 1 mM iodoacetic acid, and 1 mM benzamidine-HCl to prevent degradation of the Fc receptors.

The dialyzed extract was applied to a column of human IgG immobilized on Affi-gel 15 which had been prewashed with 3 M MgCl$_2$ and then equilibrated in 20 mM Tris-HCl, pH 7.5 containing protease inhibitors. The extract was applied to the column, and unbound material was eluted by washing with the Tris-HCl buffer. Fc receptor was eluted by addition of 3 M MgCl$_2$ to the 20 mM Tris-HCl, pH 7.5 buffer. Other eluting buffers including 1% SDS solution or 0.1 M glycine-HCl, pH 2.0 were tested, but only MgCl$_2$ resulted in the recovery of significant quantities of functionally active Fc receptors.

After elution from immobilized IgG, each fraction wad dialyzed overnight against PBS containing 10 mM EDTA to facilitate the removal of Mg$^{++}$ and all samples were finally dialysed into PBS without EDTA. Each fraction was assayed for Fc receptor activity using the competitive binding assay. Fractions containing Fc receptor activity were pooled and concentrated by Amicon Ultrafiltration using a PM-10 membrane with a molecular weight cut off of 10,000 daltons. Aliquots were stored at −70° C. and maintained their Fc receptor activity for at least one year.

The size heterogeneity of the affinity purified Fc receptor was determined by electrophoresis on an SDS polyacrylamide gel followed by staining with Coomassie brilliant blue. Two protein bands were observed. The major protein band had a molecular weight of 56,000 daltons and a minor band was observed at 38,000 daltons. To determine if both bands had Fc receptor activity, a parallel SDS polyacrylamide gel was run, the separated proteins were electroblotted onto nitrocellulose and probed with the $^{125}$I labeled Fc specific probe as described elsewhere. The results of the Western blot demonstrated that the 56,000 dalton protein reacts strongly with the $^{125}$I labeled Fc specific probe, whereas the 38,000 dalton protein demonstrated only weak reactivity, FIG. 2B.

Previous studies on the isolation of the type III receptor from a group C streptococcus also revealed the presence of a number of distinct molecular weight forms of Fc receptor activity. Each protein receptor was shown to be antigenically related which suggested that a single form of Fc receptor was present, but yielded differing forms depending on the method of extraction. In order to test whether the Fc receptor bands in the heat extract of the group A streptococcus (FIG. 2) were antigenically related, the heat extract was affinity purified on a column of immobilized chicken anti-Fc receptor antibody. This antibody was prepared against a single form of the Fc receptor isolated from an SDS polyacrylamide gel as described elsewhere. When the heat extract was affinity purified by binding to this specific affinity column and then eluted with 3M $MgCl_2$ the 56,000 and 38,000 dalton Fc receptor proteins were both recovered in a functionally active form.

Comparison of the type I, type II, and type III Fc receptors

Fc receptors isolated from *Staphylococcus aureus* (type I), by trypsin treatment of a group C streptococcal strain 26RP66 (type III), and by heat extraction of the group A streptococcal strain 64/14/HRP (type II) were electrophoresed on an SDS polyacrylamide gel, electroblotted onto nitrocellulose and probed with the $^{125}I$ labeled Fc specific probe. The results demonstrate that the group A streptococcal (type II) Fc receptor differs from both staphylococcal protein A (type I) and the group C streptococcal Fc receptor (type III). The type I receptor and the type III receptor have molecular weights of 52,000 daltons and 40,000 daltons respectively. The type II receptor, however, is larger than the other receptors with a major molecular weight band at 56,000 daltons and a minor band at 38,000 daltons.

The antigenic relationship between the type I, II and III bacterial Fc receptors was tested using monospecific chicken antibodies to each receptor type. Each antibody was tested at a number of concentrations for its ability to inhibit the binding of 125I labeled human IgG to a fixed concentration of the group A streptococcal strain 64/14/HRP. The results indicate that only the antibody against the type II Fc receptor could inhibit the binding of $^{125}I$ labeled human IgG to strain 64/14/HRP. Antibodies against the type I Fc receptor could not inhibit the binding of $^{125}I$ labeled human IgG to the group A strain 64/14/HRP or to the group C Fc receptor-rich strain 26PP66 but could completely inhibit the binding of the labeled immunoglobulin to the *Staphylococcus aureus* Cowan strain. Similarly, the antibody to the type III receptor failed to inhibit binding of $^{125}I$ human IgG to either the group A streptococcal strain 64/14/HRP or to the *Staphylococcus aureus* Cowan strain while totally inhibiting the binding of labeled immunoglobulin to the Fc receptor-rich group C streptococcus 26RP66. No inhibition of binding was observed to any bacterial strain when normal chicken immunoglobulins were added.

EXAMPLE 1

Samples containing each of the Fc rceptors were applied to 10% sodium dodecyl sulfate-polyacrylamide gels and electrophoresed in tris-glycine buffer, pH 8.3 for 16 hours at 40 V according to the method of Laemmli, Nature, Vol. 227, pp. 780-785 (1970), the disclosure of which is incorporated by reference herein. Gels were equilibrated in 25 mM tris, 192 mM glycine, pH 8.3 and 20% v/v methanol (transfer buffer) for 30 min. The separated proteins were transferred to nitrocellulose by electroblotting and parallel gels were probed with $^{125}I$ labeled human $IgG_1$, $IgG_2$, $IgG_3$ or $IgG_4$ according to the method of Yarnall et al, J. Microbiol. Meth., Vol. 3, pop. 83-93 (1984), the disclosure of which is incorporated by reference herein. A piece of nitrocellulose previously soaked in the transfer buffer was placed on top of the gel. The gel and nitrocellulose were sandwiched between 2 pieces of Whatman 3 mm paper and placed in a Bio-Rad trans blot apparatus with the nitrocellulose oriented between the anode and the gel. Electroblotting was at 70 volts for 3 hours in the above buffer. After electroblotting, the nitrocellulose was washed in veronal buffered saline containing 0.25% gelatin and 0.25% Tween-20 for 1 hour with four 250 ml changes. The nitrocellulose was probed for 3 hours in the washing buffer containing $2 \times 10^5$ cpm/ml $^{125}I$ human IgG of the appropriate subclass. After probing the nitrocellulose was washed four times in 0.01 M EDTA, 1 M NaCl, 0.25% gelatin, and 0.25% Tween-20 for 15 min. each and allowed to air dry. Autoradiography was carried out by exposure of the blot for 3 days at $-70°$ C. to Kodak XAR-5 film using an intensifying screen.

The results of a typical experiment are set forth in FIG. 1A, 1B, 1C and 1D which depicts the IgG subclass reactivity of the Fc receptors tested.

In FIG. 1, lane 1 contains 20 ng of the type I receptor (Staphylococcal Protein A). Lane 2 contains 100 ng of the type III Fc receptor, and Lane 3 contains 4,000 ng of the type II Fc receptor. Panel A is the result from blots probed with $^{125}I$ $IgG_1$. Panel B is the result from blots probed with $^{125}I$ $IgG_2$. Panel C is the result from blots probed with $^{125}I$ $IgG_3$. Panel D is the result from blots probed with $^{125}$ $IgG_4$.

The type I Fc receptor, protein A, contained one major protein band with an $M_r$ of approximately 56,000 and a minor band with an $M_r$ of approximately 38,000. The major 56,000 band reacted with human $IgG_1$, $IgG_2$, and $IgG_4$ but failed to react with human $IgG_3$. The minor 38,000 dalton protein reacted only with human $IgG_3$. The type III Fc receptor demonstrated a single protein band with an $M_r$ of approximately 40,000 and this protein reacted with all four human IgG subclasses.

The results set forth in FIG. 1 indicate that there are two distinct type II Fc receptors associated with the group A streptococcus that account for the reactivity with human IgG subclasses; the first receptor reacting with $IgG_1$, $IgG_2$, and $IgG_4$ with a second, unique receptor that reacted only with human $IgG_3$. Neither of these type II Fc receptors reacted with a monospecific chicken anti-protein A antibody, or with a monospecific chicken anti-type III Fc receptor antibody, indicating that they were antigenically unrelated to either of the other types of bacterial Fc receptors.

EXAMPLE 2

Figure 1A:
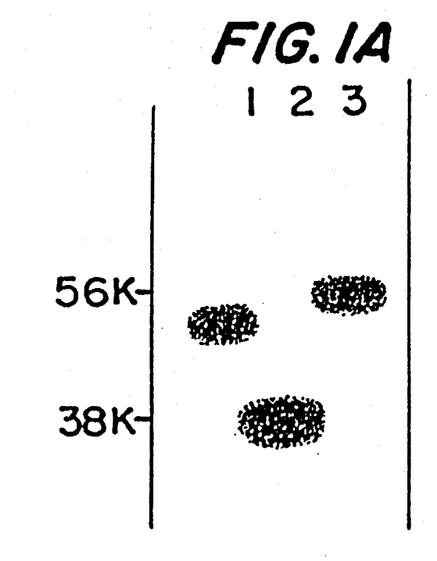
Figure 1B:
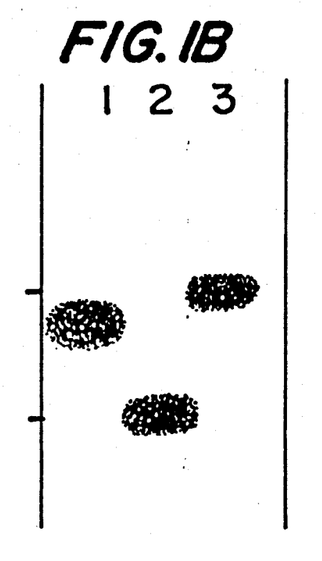
Figure 1C:
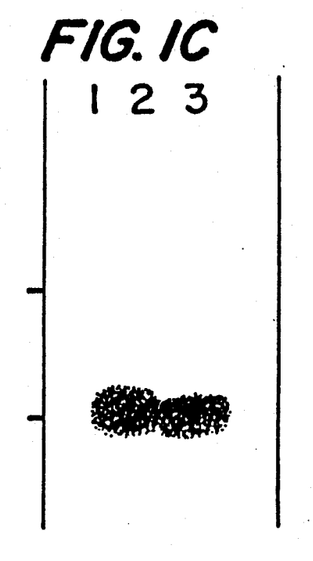
Figure 1D:
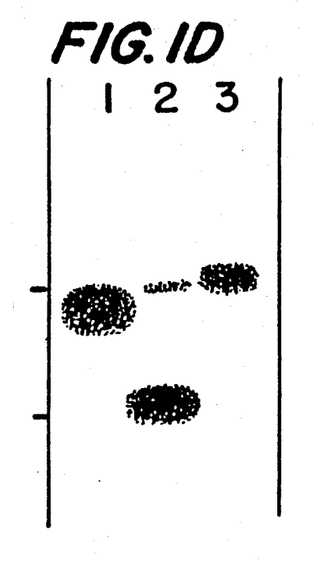
Figure 2A:
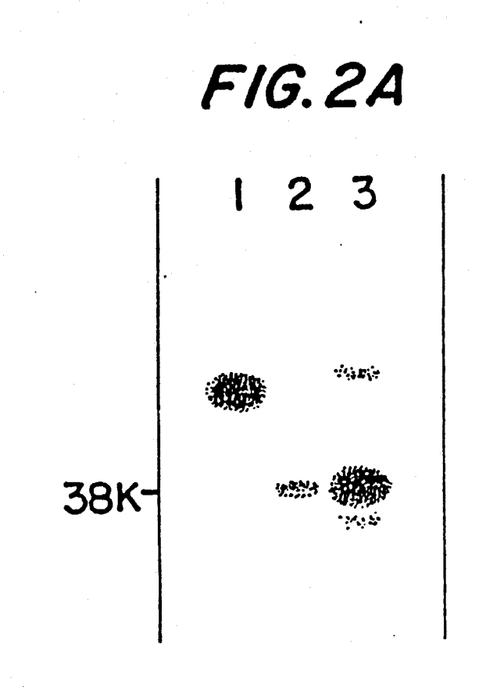
Figure 2B:
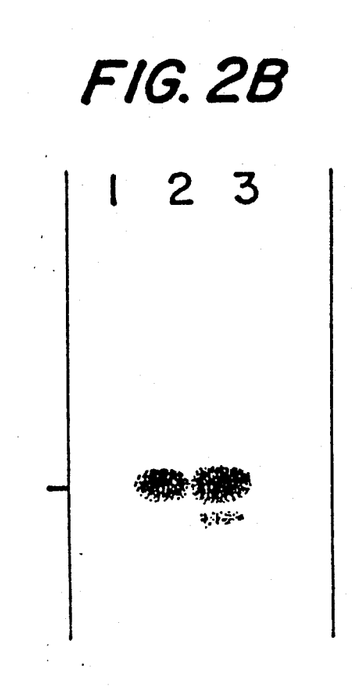
Figure 2C:
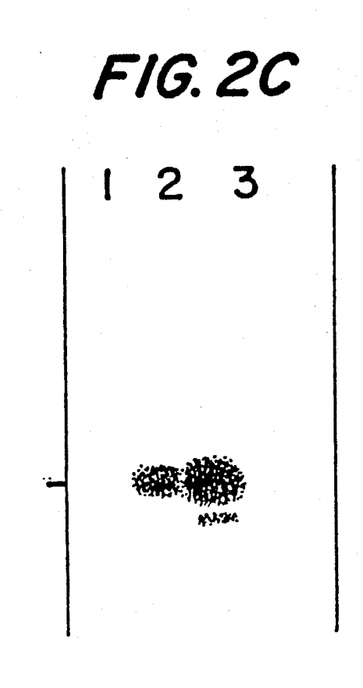

To determine whether the observed reactivity of the type II receptor with $IgG_3$ (FIG. 1) was unique to the labeled myeloma probe being used, the example was repeated using two other human $IgG_3$ myeloma proteins provided by the World Health Organization Immunoglobulin Subcommittee. The results shown in FIG. 2A, 2B and 2C indicate that all three human $IgG_3$ samples reacted with the minor $M_r$ 38,000 protein in the heat extracts of the group A streptococcus. One of the $IgG_3$ samples was found to react with the type I receptor (staphylococcal protein A) and this particular sample of IgG$_3$ also reacted with the major M$_r$ 56,000 protein as well as the minor Mr 38,000 protein in the group A extract (FIG. 2, panel A).

Lane 1 contains 20 ng of the type I receptor. Lane 2—100 ng of the type III receptor and Lane 3 contains 4,000 ng of the type II receptor. Samples were electrophoresed on parallel SDS polyacrylamide gels, electroblotted onto nitrocellulose, and each blot was probed with a different $^{125}$I labeled myeloma IgG$_3$ protein as described for FIG. 1. Autoradiography was carried out by exposure of the blot for 24 hours at −70° C. to x-ray film using an intensifying screen. Panel A represents a blot probed with a $^{125}$I IgG$_3$. Panel B represents a blot probed with a $^{125}$I IgG$_3$. Panel C represents a blot probed with a $^{125}$I IgG$_3$.

EXAMPLE 3

Figure 3:
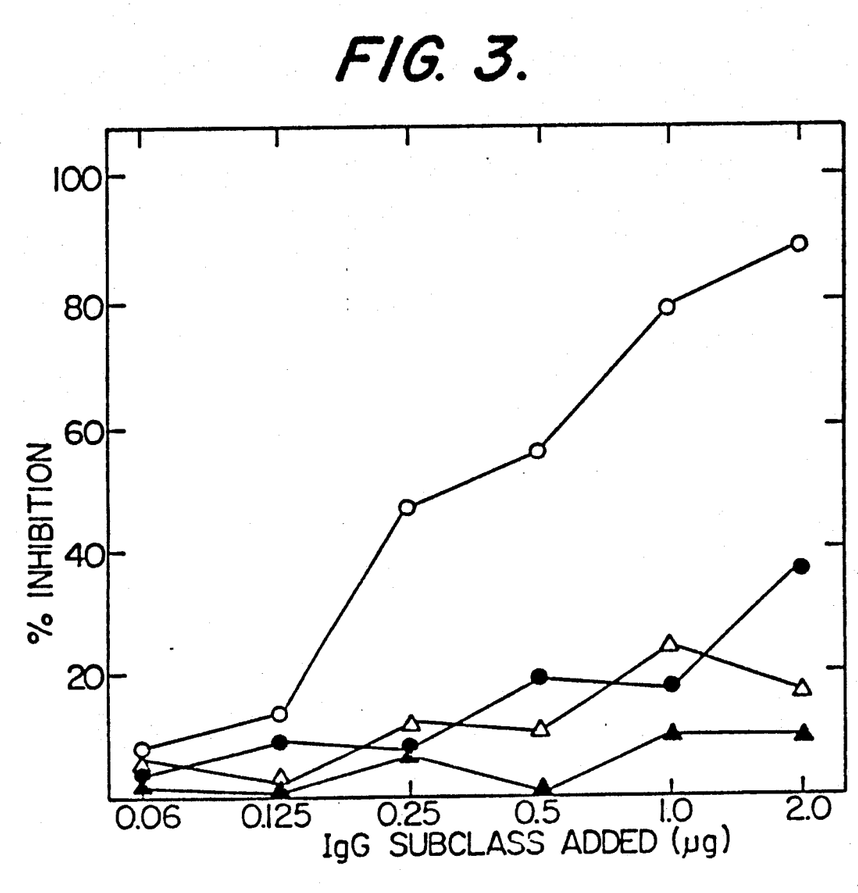

The generalized IgG$_3$ reactivity of the factor of the invention was further confirmed in inhibition studies using either unlabeled subclass standards or human serum depleted of IgG$_1$, IgG$_2$ and IgG$_4$ by exhaustive absorption with immobilized protein A.. The results are set forth in FIG. 3 wherein:

●−●=IgG$_1$
▲−▲=IgG$_2$
○−○=IgG$_3$
▲−▲=IgG$_4$.

Approximately $1 \times 10^7$ of the Fc receptor-rich group A streptococci, were incubated at 37° C. for one hour with the indicated amounts of each human IgG subclass. Following incubation, each mixture was dotted onto a piece of nitrocellulose previously soaked in 25 mM tris, 192 mM glycine, pH 8.3 and 20% v/v methanol using the Bio-Rad bio-dot microfiltration apparatus. After each well was washed with the above buffer, the nitrocellulose was removed and washed in veronal buffered saline containing 0.25% gelatin and 0.25% Tween-20 (wash buffer) for one hour with four 250 ml changes. The nitrocellulose was probed for three hours in the wash buffer containing $2 \times 10^5$ cpm/ml $^{125}$I labeled human IgG$_3$. After probing the nitrocellulose was washed four times in 0.01 M EDTA, 1M Na Cl, 0.25% gelatin and 0.25% Tween-20 and allowed to air dry. The nitrocellulose was cut into sections that contained an individual well and the cpm associated with each section of nitrocellulose was determined using an LKB autogamma counter and the percent inhibition of $^{125}$I IgG$_3$ binding to the bacteria was calculated.

Any sample containing IgG$_3$ could inhibit the binding of the $^{125}$I labeled human IgG$_3$ to the type II receptor-positive group A streptococcus by greater than 90%, while equimolar concentration of IgG$_1$, IgG$_2$ or IgG$_4$ showed less than 20% inhibition (FIG. 3). All of the samples of unlabeled IgG$_3$ tested were capable of inhibiting the binding of the labeled IgG$_3$, with the most efficient inhibitor being the sample that was also used to prepare the labeled probe. In similar studies, addition of the unlabeled, isolated type III receptor inhibited the binding of labeled IgG$_3$ to the group A streptococcus. This result demonstrates that the immunoglobulin binding site for the type II and III receptors on human IgG$_3$ are either identical or closely related domains within the Fc regions.

EXAMPLE 4

Inhibition of Binding of $^{125}$I-labeled Human IgG or Human IgG Subclass 3 to Group A Streptococcal Strain 64/14/HRP by a Monospecific Antibody Against the Purified Type II Fc Receptor To determine whether the IgG$_3$ and IgG$_1$, IgG$_2$, IgG$_4$ receptors were antigenically related, antibodies to each of the purified receptors were prepared in chickens. The ability of each antibody to inhibit binding of $^{125}$I labeled IgG$_3$ (○−○) or $^{125}$I labeled IgG$_1$, IgG$_2$ and IgG$_4$ (●−●) to the Fc receptor with 64/14/HRP group A streptococcal strain was tested. See FIGS. 4A and 4B. A standard number of group A streptococcal strain 64/14/HRP was incubatd for 1.5 hr. at 37° C. with 20,000 cpm of $^{125}$I labeled human IgG or $^{125}$I labeled human IgG$_3$ in the presence of the indicated amounts of the monspecific chicken anti-type IIa (M$_r$ 56,000 receptor) panel A or the monospecific chicken anti-type IIb) M$_r$ 38,000) Panel B. The bacteria were pelleted by centrifugation at 1000×g for 10 min. and washed twice with 2 ml veronal buffered saline containing 0.01M EDTA and 0.1% gelatin. The radioactivity associated with the bacteria was determined in an LKB Autogamma Counter and the percent inhibition calculated. The results in FIGS. 4A and 4B demonstrate that both receptors were antigenically related.

Figure 4A:
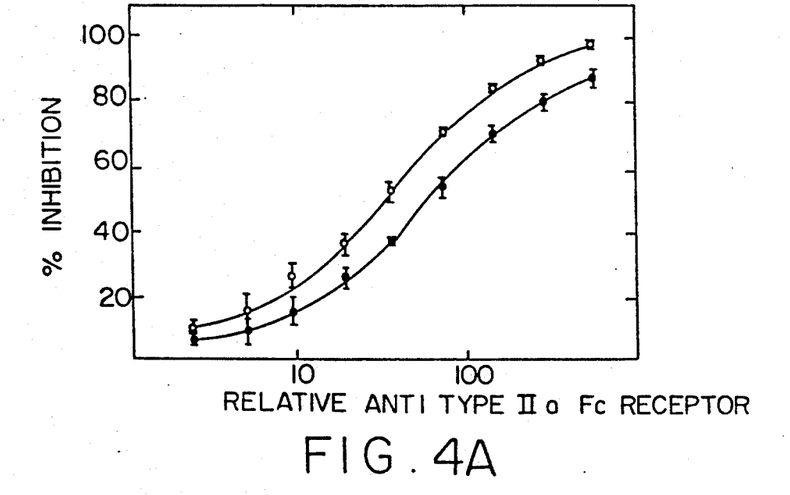
Figure 4B:
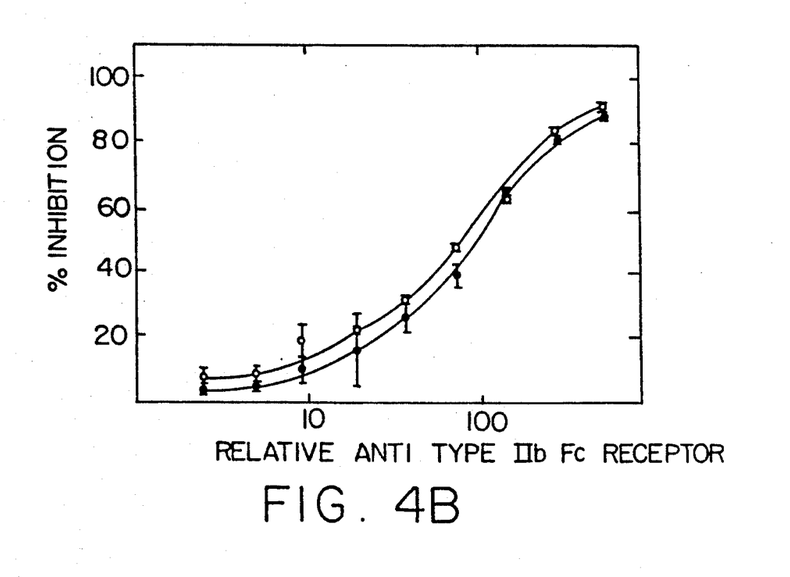

Similar results were obtained using antibody prepared against the 56,000 dalton receptor (Panel A) or the 38,000 dalton receptor (Panel B). When compared to the receptors on the Staphylococcus aureous Cowan Strain (type I) or to the type III Fc receptor on Group C streptococci strain 26RP66 they were shown to be antigenically distinct.

Figure 5:
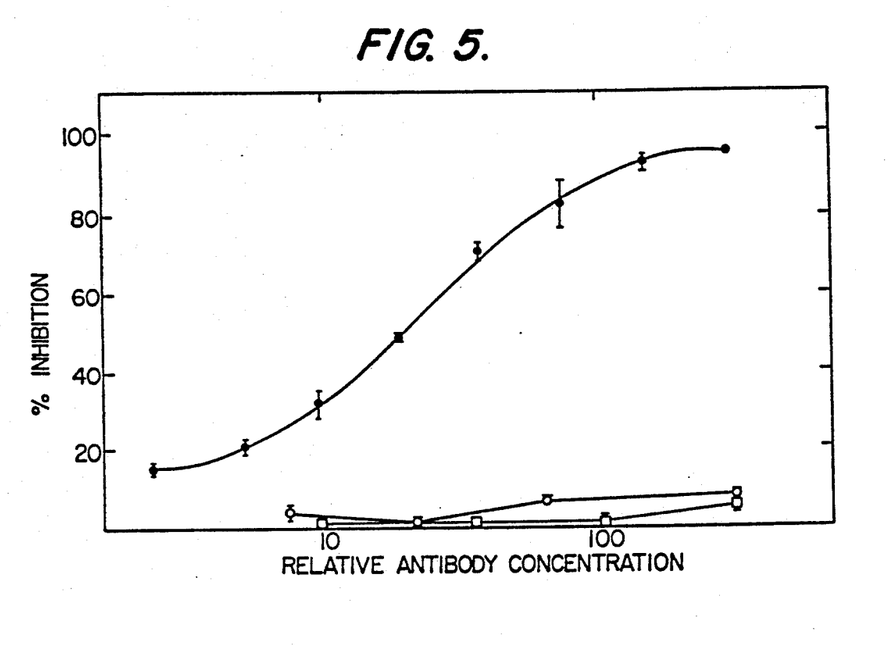

FIG. 5 depicts the inhibition of binding of $^{125}$I human IgG to 64/14/HRP by antibody against the type I receptor (□−□), the type II receptor (●−●), or the type III receptor (○−○). A relative antibody concentration of 100 for the type I antibodies inhibits the binding of $^{125}$I human IgG to the Staphylococcus aureus Cowan I strain by 94% and inhibits the binding of $^{125}$I human IgG to the group C streptococcal 26RP66 strain by less than 10%.

A relative antibody concentration of 100 for the type III antibody inhibits the binding of $^{125}$I human IgG to the group C streptococcal 26RP66 strain by less than 10%.

A relative antibody concentration of 100 for the type III antibody inhibits the binding of $^{125}$I human IgG to the Staphylococcus aureus Cowan strain by less than 10% and inhibits the binding of $^{125}$I human IgG to the group C streptococcal 26RP66 strain by 92%.

EXAMPLE 5

Comparison of the Binding of Human IgG Subclasses as a Function of pH

The binding of each radiolabeled human IgG subclass to the type II receptor positive 64/14/HRP substrain was tested. This bacteria express both the specific IgG$_3$ receptor and the IgG$_1$, IgG$_2$, IgG$_4$ receptor on its surface. IgG$_3$ bound to this bacteria via the IgG$_3$ specific receptor with two pH optima: the first at around pH 3 and the second in the pH range of 6 to 9 All of the other subclasses (i.e., IgG$_1$, IgG$_2$ and IgG$_4$) bound to their respective receptor with a single pH optimum between 6 and 9.

Figure 6:
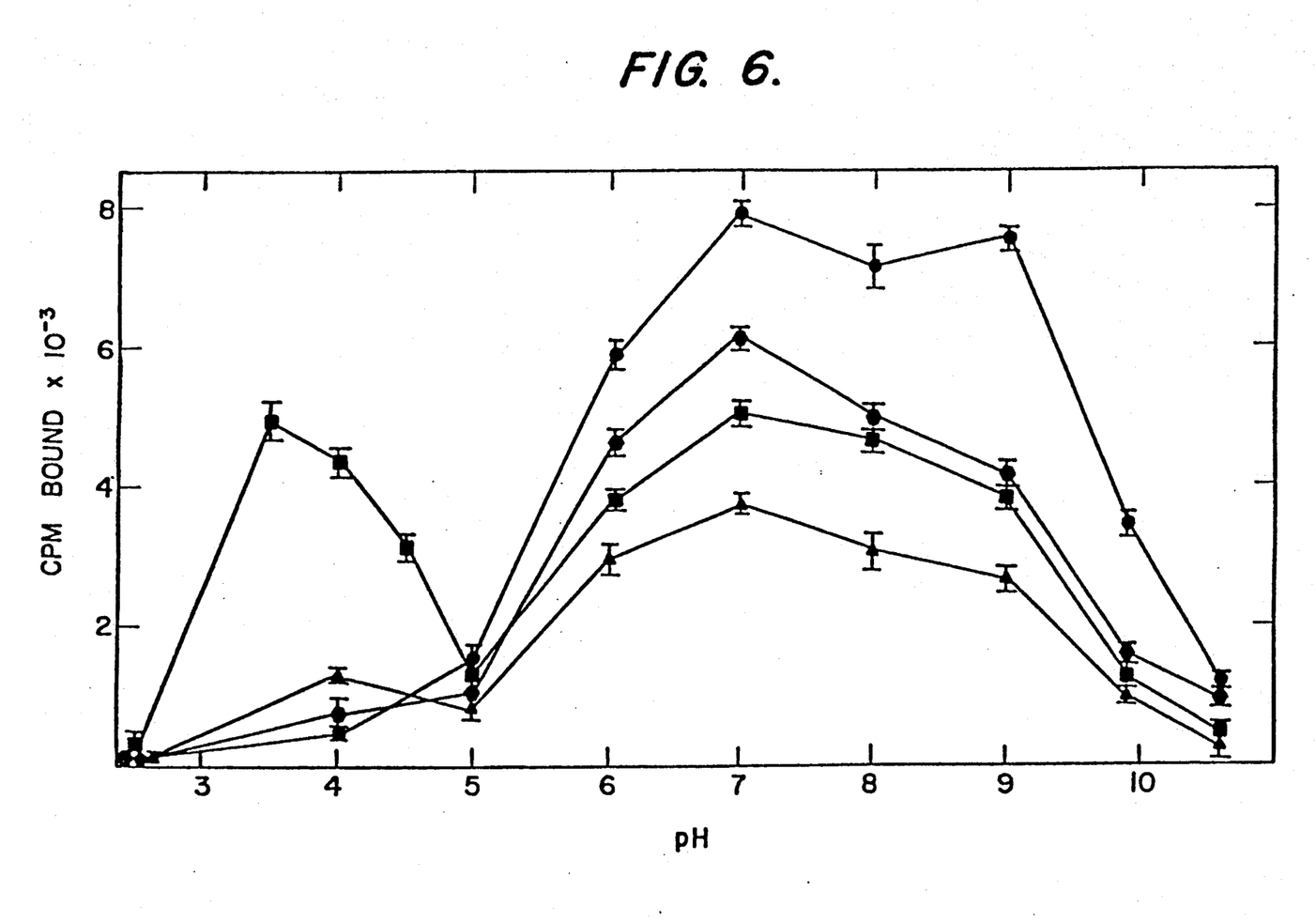

A standard number of group A streptococci was incubated for 1 hr. with 37° C. with the appropriate $^{125}$I labeled human IgG subclass at the indicated pH. Buffers used included glycine, pH 2.5, acetate, pH 3.5–5.0, phosphate, pH 6, tris, pH 7–8, and glycine, pH 9–10.5. After incubation, the bacteria were pelleted by centrifugation at 1000×g for 10 min. and washed twice with 2 ml veronal buffered saline containing 0.01M EDTA and 0.1% gelatin. The radioactivity associated with the bacteria was determined in an LKB autogamma counter. See FIG. 6 wherein:

● — ● = $^{125}$I IgG$_1$
● — ● = $^{125}$I IgG$_2$
■ — ■ = $^{125}$I IgG$_3$
● — ● = $^{125}$I IgG$_4$.

EXAMPLE 6

This example demonstrates the ability of a variety of dipeptides to inhibit the binding of radiolabeled human IgG to bacteria expressing type I, type II or type III receptors.

*Staphylococcus aureus* Cowan I served as the representative type I Fc receptor-positive strain. The group A streptococcal strain 64/14/HRP served as a representative type II Fc receptor-positive strain. The group C streptococcal strain 26RP66 served as a representative type III Fc receptor-positive strain. All strains were grown as stationary cultures in Todd Hewitt broth (Difco) for 18–24 hr at 37° C., harvested by centrifugation and washed in phosphate buffered saline (PBS), pH 7.2.

Glycyl-L-tyrosine, glycyl-L-histidine, glycyl-glycine, glycyl-DL-leucine, glycyl-DL-phenylalanine, and L-histidine were utilized in the tests.

Stock human IgG was prepared by chromatography of normal human serum on DEAE cellulose. Aliquots were stored at −70° C. until use.

Purified IgG or IgG subclasses were iodinated by mild lactoperoxidase method using enzyme beads. The IgG routinely had a specific activity of 0.3 m Ci/mg.

The detection of Fc-reactive proteins on the surface of bacteria was determined by the ability of the bacteria to bind $^{125}$I-labeled IgG as follows: Briefly, a stock preparation of bacteria was standardized to bind approximately 75% of the 20,000 cpm of labeled IgG added at pH 7.0. Following standardization for the Fc receptor activity, aliquots of bacteria were incubated with $^{125}$I-labeled IgG and the indicated amount of the dipeptides for 1.5 hr. at 37° C. The bacteria were pelleted by centrifugation at 1000×g for 5 min and washed twice with 2 ml of VBS containing 0.01M EDTA and 0.1% gelatin (EDTA-gel). The radioactivity associated with the bacteria was determined in an LKB autogamma counter. The cpm bound to the bacterial pellet were expressed as percent of maximum cpm bound.

The binding of labeled human IgG to either the standardized type I, type II or type III Fc receptor-positive bacteria in the presence or absence of glycyl-glycine, glycyl-phenylalanine, glycyl-leucine, glycyl-tyrosine and glycyl-histidine was tested over a wide concentration range. See FIG. 7.

Figure 7A:
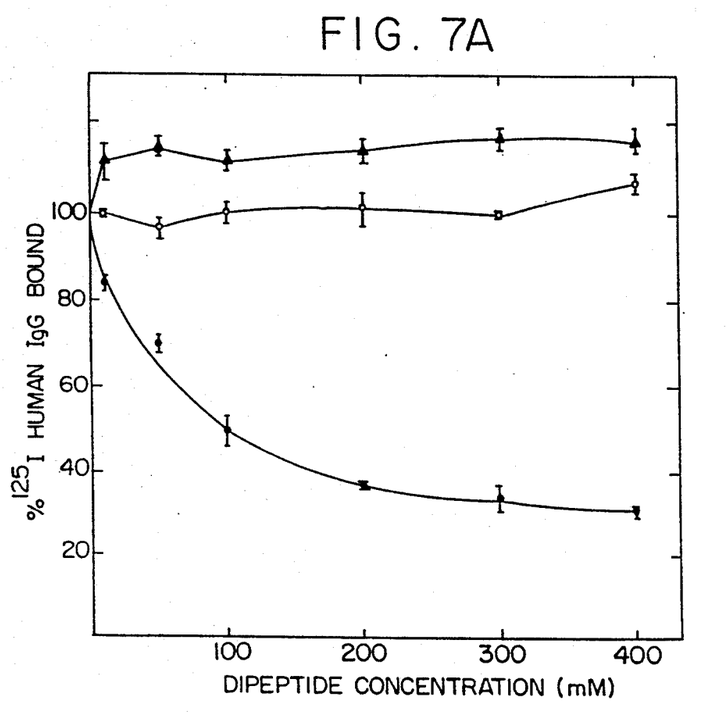
Figure 7B:
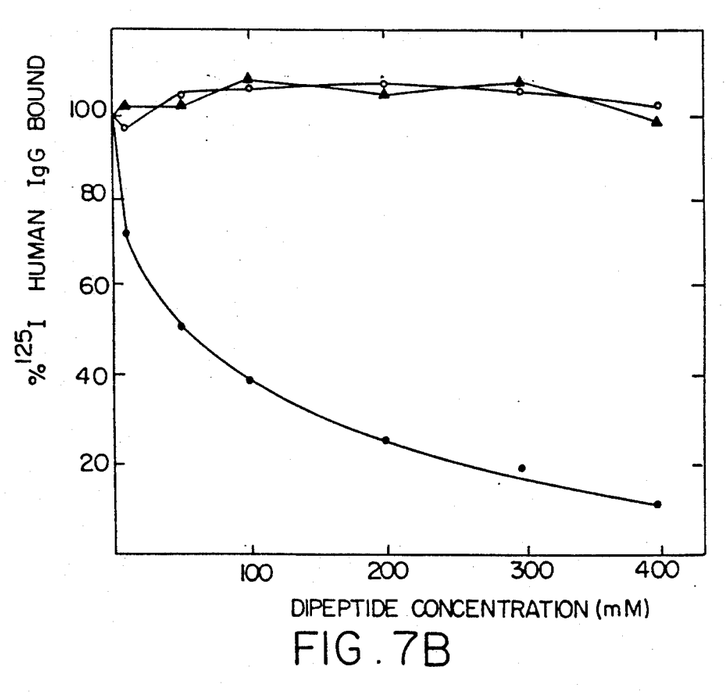
Figure 8A:
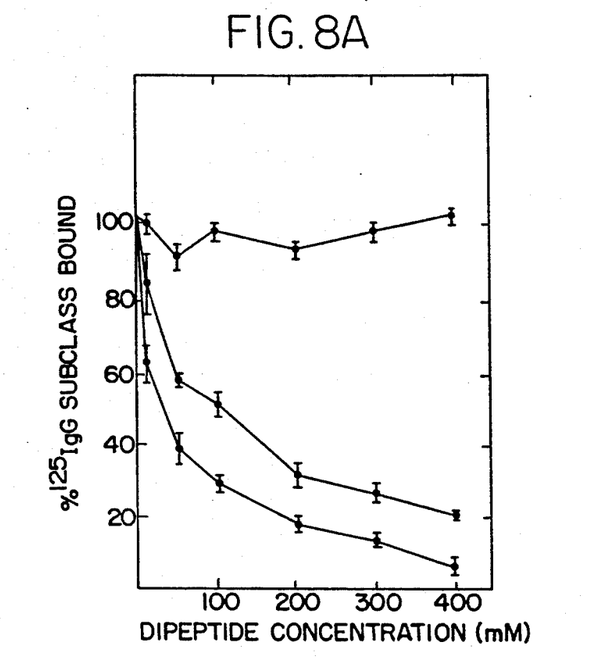
Figure 8B:
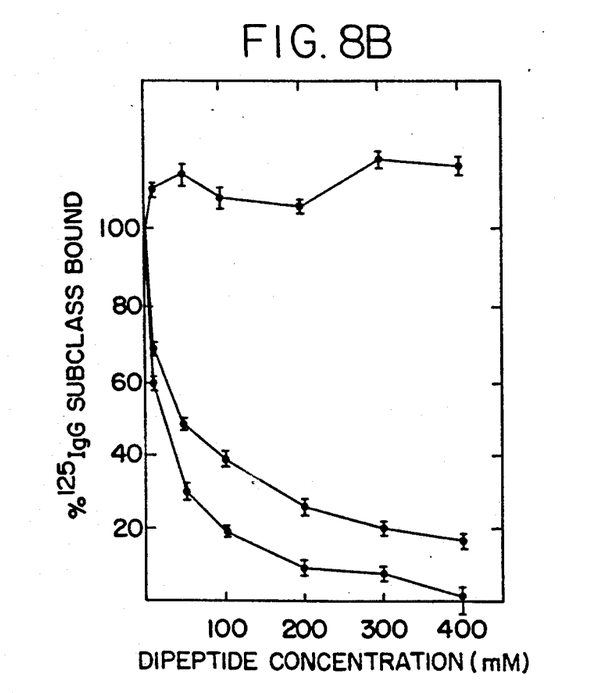
Figure 8C:
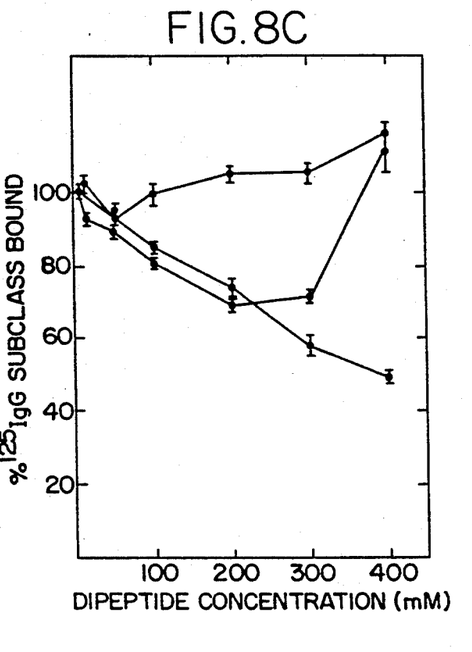
Figure 8D:
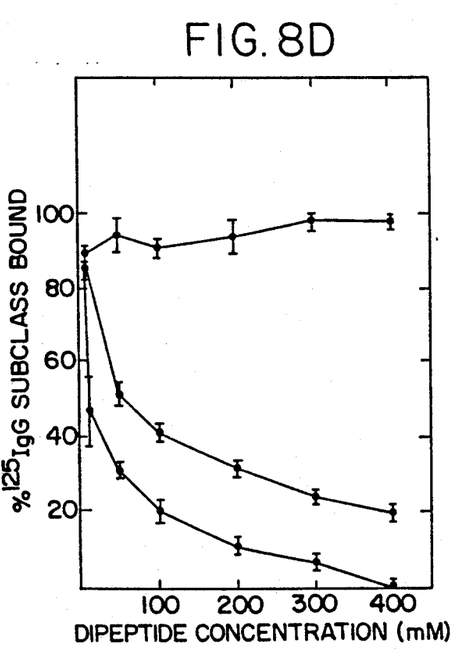

A standard number of *Staphylococcus aureus* Cowan 1 strain (▲—▲), group C streptococcal strain 26RP66 (○—○), or the group A streptococcal strain 64/14/HRP (●—●) was incubated for 1.5 hr. at 37° C. with 20,000 cpm of $^{125}$I labeled human IgG in the presence of the indicated amounts of dipeptide. The bacteria were pelleted by centrifugation at 1000×g for 10 min. and washed twice with 2 ml of veronal buffered saline containing 0.01 M EDTA and 0.1% gelatin. The radioactivity associated with the bacteria was determined in an LKB autogamma counter. The cpm bound to the bacterial pellet were expressed as percent of maximum cpm bound.

In FIG. 7, Panel A represents the results obtained with glycyl-L-tyrosine. Panel B represents the results obtained with glycyl-L-histidine.

In the next series of experiments, the ability of the inhibitory dipeptides, glycyl-tyrosine and glycyl-histidine, were tested for their ability to inhibit the binding of each labeled human IgG subclass to the type II receptor-positive 64/14/HRP bacteria. Glycyl-glycine was also included as a negative control.

A standard number of group A streptococci was incubated for 1.5 hr. at 37° C with 20,000 cpm of the appropriately $^{125}$I-labeled human IgG subclasses in the presence of varying concentrations of dipeptide. The bacteria were pelleted by centrifugations of 1000×g for 10 min. and washed twice with 3 ml of veronal buffered saline containing 0.01 M EDTA and 0.1% gelatin. The radioactivity associated with the bacteria was determined in an LKB autogamma counter. The cpm bound to the baterial pellet were expressed as percent of maximum cpm bound. See FIG. 8 wherein Panel A represents the results obtained from the binding of $^{125}$I IgG$_1$. Panel B represents the results obtained from the binding of $^{125}$I IgG$_2$. Panel C represents the results obtained from the binding of $^{125}$I IgG$_3$. Panel D represents the results obtained from the binding of $^{125}$I IgG$_4$.

(●—●) represents glycyl-glycine.
(■—■) represents glycyl-L-histidine.
(▲—▲) represents glycyl-L-tyrosine.

Glycyl-tyrosine and glycyl-histidine were found to efficiently inhibit the binding of labeled $^{125}$I human IgG$_1$, IgG$_2$ and IgG$_4$ to the bacteria. By contrast, minimal inhibition of labeled IgG$_3$ binding was observed in the presence of either dipeptide.

The results presented in FIG. 8 suggest the existence of two distinct Fc receptors on the surface of the group A streptococcal strain 64/14/HRP, one receptor binds human subclasses IgG$_1$, IgG$_2$ and IgG$_4$ and a second receptor which recognizes human IgG$_3$ exclusively.

In the next series of experiments the effect of histidine, glycyl-histidine or glycyl-tyrosine on the binding of labeled pig or rabbit IgG was tested. Similar results were obtained with each inhibitor and the results using histidine are presented in FIG. 9. These results demonstrate that histidine inhibited the binding of rabbit, pig or human IgG and suggest that binding of the Fc region of pig and rabbit IgG occurs via the type IIa receptor in a similar dose dependent manner and that the interaction occurs in a similar way.

Figure 9:
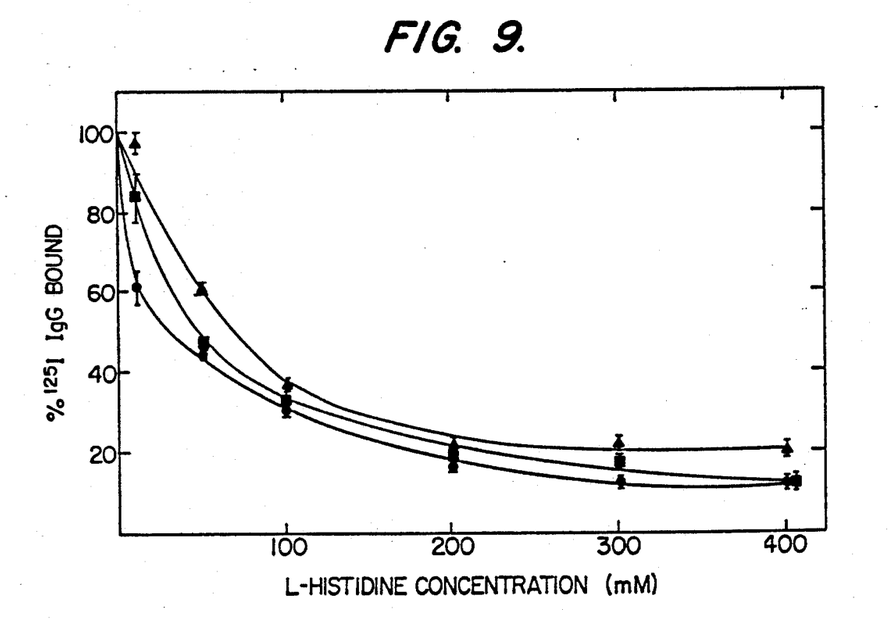

In FIG. 9, the effect of L-histidine on the binding of $^{125}$I-labeled rabbit, pig or human IgG to group A strain 64/14/HRP is demonstrated. A standard number of group A streptococci was incubated for 1.5 hr. at 37° C. with 20,000 cpm of the appropriately $^{125}$I-labeled species IgG in the presence of the indicated amounts of histidine. The bacteria were washed as described above. The cpm bound to the bacterial pellet were expressed as percent of maximum cpm bound. In FIG. 9, (●—●) represents $^{125}$I human IgG; (▲—▲) represents $^{125}$I pig IgG; and (■—■) represents rabbit IgG.

The inhibition of IgG binding of labeled human IgG to type II Fc receptor positive bacteria was observed in the presence of glycyl-tyrosine, or glycyl-histidine but not in the presence of any other dipeptide. Analysis of the inhibition of binding of individual labeled human IgG subclasses indicated the presence of two distinct Fc receptors associated with the type II Fc receptor-positive group A streptococcal strain being tested. Glycyl-tyrosine, glycyl-histidine or histidine alone inhibited binding of labeled human $IgG_1$, $IgG_2$, $IgG_4$, pig or rabbit IgG but demonstrated minimal inhibition of the binding of human $IgG_3$. No inhibition of labeled human IgG binding to type I or type III Fc receptor positive bacteria was observed with any of the dipeptides tested.

The entire disclosures of each of the literature and patent references cited and discussed hereinabove are incorporated herein by reference.

The $IgG_3$ specific receptor is useful for measuring $IgG_3$ specific responses to a variety of different antigens, e.g., bacterial antigens associated with such organisms as Brucella or Pneumococci and any vial antigen for which the purified material was available. The $IgG_3$ specific receptor is also used in methods for probing for $IgG_3$ specific myelomas and for the isolation of purification of human $IgG_3$.

Employing both the $IgG_3$ specific receptor and the $IgG_{1,2,4}$ specific receptor to measure separately specific antibody responses to a variety of different infections the ratio of antibodies of $IgG_1$, $IgG_2$, $IgG_4$ to those of $IgG_3$ will be of value for monitoring disease states. This would be particularly true for a number of parasitic infections, e.g., filaria infections, where it has been reported that there is a predominant $IgG_3$ response to parasite infection without a change in the responses of $IgG_1$, $IgG_2$ or $IgG_4$. Consequently, by measuring the ratio of $IgG_3$ antibodies to the total $IgG_1$, $IgG_2$ and $IgG_4$ anti-filarial antibodies, a decreased ratio would be indicative of infection.

What is claimed is:

1. A type II proteinaceous antigenic factor derived from a group A streptococcus which is a receptor for the Fc region of human $IgG_1$, $IgG_2$ and $IgG_4$ and which exhibits a major diffuse protein band on polyacrylamide gel electrophoresis and which has a molecular weight of approximately 56,000 daltons.

2. The factor of claim 1 labeled with a radioisotopoe, enzyme or electron dense ligand.

3. The labeled factor of claim 2 wherein said radioisotope is $^{125}I$, $^{131}I$, $^{3}H$, $^{14}C$ or $^{35}S$.

4. The labeled factor of claim 2 wherein said enzyme is lactoperoxidase, horse-radish peroxidase, alkaline phosphates, or glucose oxidase.

5. The labeled factor of claim 2 wherein said electron dense ligand is ferritin, gold or horse-radish peroxidase.

6. The factor of claim 1 immobilized on an inert support.

* * * * *

UNITED STATES PATENT AND TRADEMARK OFFICE
CERTIFICATE OF CORRECTION

PATENT NO. : 5,071,756

DATED : December 10, 1991

INVENTOR(S) : Michael D.P. Boyle, Michele Yarnall

It is certified that error appears in the above-identified patent and that said Letters Patent is hereby corrected as shown below:

| | |
|---|---|
| Column 2: | line 11: "a non-reactive IgG3" should read --a non-reactive $IgG_3$--. |
| Column 6: | line 1: "The I9G" should read --The IgG--; line 51: "adjuvant Eggs were" should read --adjuvant. Eggs were--. |
| Column 9: | line 42: "the binding of 125I" should read --the binding of $^{125}I$--. |
| Column 11: | line 3: "the minor Mr 38,000" should read --the minor $M_r$ 38,000--. |
| Column 12: | line 65: "6 to 9 All" should read --6 to 9. All--. |
| Column 13: | line 13: "●-● = $^{125}I$ IgG$_2$" should read --●-● = $^{125}I$ $IgG_2$--; line 15: "●-● = $^{125}I$ IgG$_4$" should read --▲-▲ = $^{125}I$ $IgG_4$--. |
| Column 16: | line 24: "phosphates" should read --phosphatase--. |

Signed and Sealed this

Thirteenth Day of April, 1993

*Attest:*

STEPHEN G. KUNIN

*Attesting Officer*   Acting Commissioner of Patents and Trademarks